US011261205B2

(12) United States Patent
Kapsner et al.

(10) Patent No.: US 11,261,205 B2
(45) Date of Patent: *Mar. 1, 2022

(54) OXAZOLIDINONE-QUINOLONE HYBRID ANTIBACTERIAL FOR THE PARENTERAL TREATMENT OF PROPHYLAXIS OF BACTERIAL DISEASES

(71) Applicant: Morphochem GmbH, Munich (DE)

(72) Inventors: Thomas Kapsner, Gröbenzell (DE); Axel Dalhoff, Wuppertal (DE); Thomas Gramatte, Dresden (DE)

(73) Assignee: Morphochem GmbH, Munich (DE)

( * ) Notice: Subject to any disclaimer, the term of this patent is extended or adjusted under 35 U.S.C. 154(b) by 41 days.

This patent is subject to a terminal disclaimer.

(21) Appl. No.: 16/908,244

(22) Filed: Jun. 22, 2020

(65) Prior Publication Data

US 2020/0392168 A1    Dec. 17, 2020

Related U.S. Application Data

(63) Continuation of application No. 14/894,400, filed as application No. PCT/EP2014/001253 on May 9, 2014, now Pat. No. 10,723,746.

(30) Foreign Application Priority Data

May 28, 2013 (EP) .................... 13002762
Dec. 10, 2013 (EP) .................... 13005745
Dec. 10, 2013 (EP) .................... 13005748

(51) Int. Cl.
*C07F 9/653* (2006.01)
*A61K 31/4709* (2006.01)
*A61K 31/4375* (2006.01)
*A61P 31/04* (2006.01)
*A61P 31/00* (2006.01)
*A61P 1/12* (2006.01)
*A61P 1/00* (2006.01)

(52) U.S. Cl.
CPC .......... *C07F 9/653* (2013.01); *A61K 31/4375* (2013.01); *A61K 31/4709* (2013.01); *A61P 1/00* (2018.01); *A61P 1/12* (2018.01); *A61P 31/00* (2018.01); *A61P 31/04* (2018.01)

(58) Field of Classification Search
CPC ......... C07F 9/633; A61P 31/00; A61P 31/04; A61P 1/00; A61P 1/12; A61K 31/4375; A61K 31/4709
See application file for complete search history.

(56) References Cited

U.S. PATENT DOCUMENTS

2008/0027040 A1*  1/2008  Hubschwerlen ........ A61P 31/04
                                                514/217.02
2009/0264342 A1   10/2009  Cottarel et al.

FOREIGN PATENT DOCUMENTS

| WO | 2002059116 A2 | 8/2002 |
| WO | 2003002560 A1 | 1/2003 |
| WO | 2003031441 A1 | 4/2003 |
| WO | 2003031443 A1 | 4/2003 |
| WO | 2003032962 A2 | 4/2003 |
| WO | 2004096221 A1 | 11/2004 |
| WO | 2005023801 A1 | 3/2005 |
| WO | 2005058888 A2 | 6/2005 |
| WO | 2007017828 A2 | 2/2007 |
| WO | 2008056335 A1 | 5/2008 |
| WO | 2008062379 A2 | 5/2008 |
| WO | 2009136379 A1 | 11/2009 |

OTHER PUBLICATIONS

Belikov, "Framacevticeskaa himia," 1993.
Cohen et al., "Clinical Practice Guidelines for Clostridium difficile Infection in Adults: 2010 Update by the Society for Healthcare Epidemiology of America (SHEA) and the Infectious Diseases Society of America (IDSA)," Infection Control and Hospital Epidemiology. 2010; 31(5): 431-455.
Dalhoff et al., "Alternative Strategies for Proof-of-Principle Studies of Antibacterial Agents," Antimicrobial Agents and Chemotherapy. 2014; 58(8): 4257-4263.
Decision on Rejection dated Jan. 10, 2019 in corresponding Chinese Patent Application No. 2014800313733 (English language translation included).
Denéve et al., "New Trends in Clostridium difficile virulence and pathogenesis," International Journal of Antimicrobial Agents. 2009; 33: S24-S28.
Gaudriault, "Deinove: DNV3681/DNV3837 Project update," ECCMID 2019, Therapeutics Pipeline Corner, Apr. 14, 2019.
Gordeev et al., "Novel oxazolidinone-quinolone hybrid antimicrobials," Bioorganic & Medicinal Chemistry Letters. 2003; 13(23): 4213-4216.
Hill, "Pharmacokinetics of drug infusions," Continuing Education in Anaesthesia, Critical Care & Pain. 2004; 4(3): 76-80.
Hubschwerlen et al., "Structure-Activity Relationship in the Oxazolidinone-Quinolone Hybrid Series: Influence of the Central Spacer on the Antibacterial Activity and the Mode of Action," Bioorganic & Medicinal Chemistry Letters. 2003; 13:4229-4233.
Hubschwerlen et al., "Design, Synthesis and Biological Evaluation of Oxazolidinone-Quinolone Hybrids," Bioorganic & Medicinal Chemistry. 2003; 11: 2313-2319.
Huien et al., "Introduction to Modern Practical Medicine," Heilongjiang Science and Technology Press. Jan. 31, 2007; p. 311.
International Search Report issued in International Application No. PCT/EP2014/001253 dated Jul. 4, 2014.
Kresken et al., "In Vitro Activity of the Novel Antibacterial MCB3681 Against Selected Gram-Positive and -Negative Bacteria Compared to Established Antibiotics," 1 page.

(Continued)

*Primary Examiner* — Timothy R Rozof
(74) *Attorney, Agent, or Firm* — Andrea L. C. Reid; Gang Wang; Dechert LLP

(57) ABSTRACT

The present invention relates to the use of oxazolidinone-quinolone hybrids for the parenteral (especially intravenous) treatment or prophylaxis of bacterial diseases. The present invention relates moreover to improved methods of administering oxazolidinone-quinolone hybrid antibacterials.

20 Claims, No Drawings

(56) References Cited

OTHER PUBLICATIONS

Miller et al., "Health Care-Associated Clostridium difficile Infection in Canada: Patient Age and Infecting Strain Type Are Highly Predictive of Severe Outcome and Mortality," Clinical Infectious Diseases. 2010; 50: 194-201.
Office Action dated Apr. 19, 2018 in corresponding Russian patent application No. 2015155645 (English language translation).
Pépin et al., "Increasing Risk of Relapse after Treatment of Clostridium difficile Colitis in Quebec, Canada," Clinical Infectious Diseases. 2005; 40: 1591-1597.
Rashid et al., "Ecological impact of MCB3837 on the normal human microbiota," International Journal of Antimicrobial Agents. 2014; 44: 125-130.
Rashid et al., "In vitro activity of MCB3681 against Clostridium difficile strains," Anaerobe. 2014; 28: 216-219.
Rashid et al., "In vitro activity of MCB3681 against Clostridium difficile strains," Poster #0802; 2014.
Rashid et al., "Ecological and pharmacodynamic effects of MCB3681 on skin, nasal, oropharyngeal and intestinal microbiota," Poster #1670; 2014.
Shiu et al., "Continuous versus intermittent infusions of antibiotics for the treatment of severe acute infections," Cochrane Database of Systematic Reviews. 2013; Issue 3, Art No. CD008481.
Voigt et al., "Mode of action of MCB3681—analysis of MCB3681 proteome signature," 2014.
Wenisch et al., "A prospective cohort study on hospital mortality due to Clostridium difficile infection," Infection. 2012; 40: 479-484.
Yoo et al., "Clostridium difficile Infections: What Every Clinician Should Know," The Permanente Journal/Summer. 2010; 14(2): 35-40.
Ziyang et al., "Manual for Poisoning First Aid," Shanghai Science and Technology Press. Jun. 30, 2007; p. 558.

* cited by examiner

OXAZOLIDINONE-QUINOLONE HYBRID ANTIBACTERIAL FOR THE PARENTERAL TREATMENT OF PROPHYLAXIS OF BACTERIAL DISEASES

The present invention relates to the use of oxazolidinone-quinolone hybrids for the parenteral (especially intravenous) treatment or prophylaxis of bacterial diseases.

According to a preferred embodiment, the present invention relates to improved methods of administering oxazolidinone-quinolone hybrid antibacterials.

According to a moreover preferred embodiment, the present invention relates to the use of oxazolidinone-quinolone hybrids for the parenteral (especially intravenous) treatment or prophylaxis of intestinal diseases which are caused by Gram-positive bacteria (e.g. *S. aureus, Enterococcus* spp.), especially Gram-positive anaerobes such as *Clostridium* spp., in particular *Clostridium difficile* and *Clostridium perfringens* (especially by *Clostridium difficile*).

Oxazolidinone-quinolone hybrids are useful antimicrobial agents effective against a variety of human and veterinary pathogens. Oxazolidinone-quinolone hybrids have already been described in the prior art (e.g. in WO 02/059116, WO 03/002560, WO 03/031443, WO 03/032962, WO 2004/096221, WO 2005/058888, WO 2007/017828, WO 2008/056335, WO 2008/062379 and WO 2009/136379).

*Clostridium difficile*, a Gram-positive, spore forming, anaerobic *bacillus*, is a leading cause of antibiotic-associated diarrhea especially in hospitals and long-term care facilities but also in low risk persons, such as healthy persons in the community, and peripartum women. *Clostridium difficile* infections can be triggered in patients e.g. as a consequence of treatment with broad spectrum antibacterials that alter the ecological balance of the commensal intestinal flora, allowing *C. difficile* proliferation and toxin production as well as *C. difficile* spore germination. Symptoms of *Clostridium difficile* infections may vary from mild diarrhea to life-threatening clinical pictures such as fulminant colitis, pseudomembranous colitis, toxic megacolon, and death. These symptoms are mainly caused by the cytotoxic effects of *C. difficile* toxin A and toxin B.

The epidemiology of *Clostridum difficile* infections (CDI) has changed over the past 15 years as the population of elderly is increasing: age >65 years is one of the most important risk factors for CDI and the majority of CDI is occurring in patients aged >65 years: from 1996 to 2009 CDI in patients >65 years increased by 200% in total (National Hospital Discharge Survey Annual files 1996-2009: http://www.cdc/nchs/nhds.htm, accessed on May 22, 2013).

Most cases of CDI are currently treated with oral administration of the antibacterials metronidazole, vancomycin or fidaxomicin. Frequency of recurrence of CDI is between 20 and 25% for metronidazole or vancomycin, and approximately 13% for fidaxomicin (Tillotson G S and Tillotson J: *Clostridium difficile*—a moving target. F1000 Medicine Reports 2011, 3:6 doi:10.3410/M3-6). Both the cure rate of oral therapy is decreasing, and the recurrence rate is increasing with the age of CDI patients (Pepin J, Alary M E, Valiquette L, Raiche E, Ruel J, Fulop K, Godin D, Bourassa C: Increasing risk of relapse after treatment of *Clostridium difficile* colitis in Quebec, Canada. Clin Infect Dis 2005; 40: 1591-1597). Furthermore, mortality of CDI patients is increasing with age (Miller M, Gravel D, Mulvey M, Taylor G, Boyd D, Simor A, Gardam M, McGeer A, Hutchinson J, Moore D, Kelly S: Health care-associated *Clostridium difficile* infection in Canada: Patient age and infecting strain type are highly predictive of severe outcome and mortality. Clin Infect Dis 2010; 50: 194-201).

Parenteral (especially intravenous) treatment or prophylaxis of CDI is preferable for the following reasons:

1) Elderly patients often have difficulties with oral administration of antibacterials, i.e. swallowing tablets, which is circumvented by parenteral (especially intravenous) treatment of CDI.

2) The clinical presentation of CDI is characterized by watery diarrhea and frequent unformed bowel movements per day. Consequently, orally administered antibacterial agents are rapidly eliminated/excreted (Yoo J, Lightner A L: *Clostridium difficile* infections: what every clinician should know. The Permanente Journal 2010; 14: 35-40). Parenteral (especially intravenous) treatment would prolong exposure of *Clostridium difficile* in the gastro-intestinal tract to the antibacterial significantly.

3) Severely ill CDI patients, e.g. with ileus or toxic megacolon, may have markedly delayed passage of orally administered antibacterial agents from the stomach to the colon resulting in low and variable concentrations of the antibacterial at the location of infection (Wenisch J M, Schmid D, Tucek G, Kuo H W, Allerberger F, Michl V, Tesik P, Laferl H, Wenisch C. A prospective cohort study on hospital mortality due to *Clostridium difficile* infection. Infection. 2012; 40(5):479-484). Parenteral (especially intravenous) treatment would secure continous exposure of *Clostridium difficile* to the antibacterial in the gastro-intestinal tract.

4) The infectious process of *C. difficile* is characterized by adherence and intestinal colonization (accessory role of several pathogenicity factors like proteolytic enzymes and adhesins) followed by production of two toxins (TcdA and TcdB) which damage the colonic mucosa, so that *C. difficile* bacteria penetrate into cells of the gastro-intestinal mucosa. Thus, the pathogenesis of CDI is characterized by growth within mucous layers and within human gastro-intestinal cells, so that the vegetative (active) forms of *C. difficile* bacteria are not readily accessible by orally administered antibacterial agents distributed within the fecal matrix. Furthermore, CDI is primarily occurring in patients having been using antibacterials for treatment of infectious diseases, e.g. urinary- or respiratory-tract infections which almost always alters the intestinal commensal microbiota, disrupts colonization resistance and may promote *C. difficile* spore germination (inactive form), vegetative cell growth, toxin production and resistance development, so that total numbers of *C. difficile* vegetative cells and spores hiding in gastro-intestinal mucus, mucosal cells, villi and microvilli, and/or crypts and glands of the gastro-intestinal tract increase significantly. These persisting vegetative bacteria and spores are not accessible by orally administered antibacterial agents, however by antibacterials administered parenterally (Deneve C, Janoir C, Poilane I, Fantinato C, Collignon A: New trends in *Clostridium difficile* virulence and pathogenesis. Int J Antimicrob Agents 2009; 33: S24-S28).

5) Treatment of recurrent CDI is difficult as approved intravenous treatment regimen alternatives to oral vancomycin and oral fidaxomicin are currently not available. However, recurrent episodes of CDI occur with increasing frequency. The first recurrent episode of CDI is usually treated with the same regimen as the first one, and subsequent recurrences are treated with tapered and/or pulsed doses of metronidazole or vancomycin (Stuart H. Cohen, M D; Dale N. Gerding, M D; Stuart Johnson, M D; Ciaran P. Kelly, M D; Vivian G. Loo, M D; L. Clifford McDonald, M D; Jacques Pepin, M D; Mark H. Wilcox, M D. Clinical Practice Guidelines for *Clostridium difficile* Infection in Adults: 2010 Update by the Society for Healthcare Epidemiology of America (SHEA) and the Infectious Diseases Society of America (IDSA). Infect Control Hosp Epidemiol 2010; 31(5):431-455). However, long term treatment with vancomycin and metronidazole has been associated with neurotoxicity (metronidazole) and nephrotoxicity (vancomycin).

Parenteral (especially intravenous) administration of a compound of Formula (I) surprisingly resulted in a pronounced effect against Gram-positive bacteria and Gram-positive anaerobes in the gastro-intestinal tract of human subjects. Furthermore, compounds of formula (I) are effective against *C difficile* in-vitro although the two pharmacophores of compounds of formula (I) are ineffective against *C difficile*. Therefore, it could not be assumed that compounds of formula (I) could affect viable counts of *Clostridium* spp. in vivo: Ciprofloxacin is neither active in vitro nor effective in vivo against anaerobes, in particular not against Gram-positive anaerobes, despite high fecal concentrations. Vice versa, linezolid is active in vitro against *C difficile* but inactive in an in vitro human gut model. The inactivity of linezolid in this model is consistent with negligibly low fecal concentrations of linezolid (0.2% of the dose are excreted via the feces).

It has been one object of the present invention to provide methods for administering therapeutically effective amounts of oxazolidinone-quinolone hybrids.

The present invention provides a method for administering an oxazolidinone-quinolone hybrid, comprising administering to a patient in need thereof an oxazolidinone-quinolone hybrid at an infusion rate of from 0.4 to 3.0 (preferably from 0.4 to 1.5; especially preferably from 0.4 to 0.75) mg/(kg body weight×h).

Moreover, the present invention provides a method for the use of an oxazolidinone-quinolone hybrid for the manufacture of a medicament for treating a bacterial infection in a patient in need thereof wherein the oxazolidinone-quinolone hybrid is administered at an infusion rate of from 0.4 to 3.0 (preferably from 0.4 to 1.5; especially preferably from 0.4 to 0.75) mg/(kg body weight×h).

Moreover, the present invention provides an oxazolidinone-quinolone hybrid for use in the treatment of a bacterial infection, said treatment comprising the administration of the oxazolidinone-quinolone hybrid at an infusion rate of from 0.4 to 3 (preferably from 0.4 to 1.5; especially preferably from 0.4 to 0.75) mg/(kg body weight×h).

Preferably, the oxazolidinone-quinolone hybrid is administered over a period of from 20 min to 24 h; preferably of from 20 min to 5 h; further preferably of from 4 h to 12 h per day at the infusion rate of the present invention. Such a daily dose can e.g. be administered once or e.g. over a period of up to 5 days, or up to 10 days or even over a period of up to 6 months or more depending on the severity of the infection.

Preferably, the oxazolidinone-quinolone hybrid is selected from the compounds described in WO02059116, WO03002560, WO03031443, WO03032962, WO2005058888, WO2005023801, WO2004096221, WO2007017828, WO2008056335, WO2008062379 and/or WO2009136379.

Further preferably, the oxazolidinone-quinolone hybrid is a compound of formula (I),

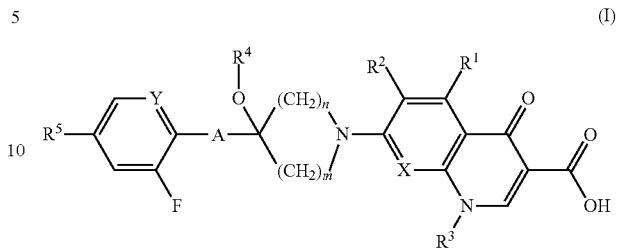

wherein
A is an alkylene group, an alkenylene group, an alkynylene group, a heteroalkylene group, a cycloalkylene group, a heterocycloalkylene group, an arylene group or a heteroarylene group all of which groups may be substituted;
X is $CR^7$ or N;
Y is $CR^6$ or N;
n is 1, 2 or 3;
m is 1, 2 or 3;
$R^1$ is H, F, Cl, Br, I, OH, $NH_2$, an alkyl group or a heteroalkyl group;
$R^2$ is H, F or Cl;
$R^3$ is H, an alkyl group, an alkenyl group, an alkynyl group, a heteroalkyl group, a cycloalkyl group, a heterocycloalkyl group, an alkylcycloalkyl group, a heteroalkylcycloalkyl group, an aryl group, a heteroaryl group, an alkylaryl group or a heteroarylalkyl group; all of which groups may be substituted with one, two or more halogen atoms like F or Cl or amino groups.
$R^4$ is a hydrogen atom, a group of formula $PO_3R^9{}_2$ or $SO_3R^{10}$ or a heteroalkyl group carrying at least one OH, $NH_2$, $SO_3R^{10}$, $PO_3R^9{}_2$ or COOH group or an ester of a naturally occurring amino acid or a derivative thereof, wherein the groups $R^9$ independently of each other are H, alkyl, cycloalkyl, aryl or aralkyl and wherein R" is H, alkyl, cycloalkyl, aryl or aralkyl;
$R^5$ is selected from following groups:

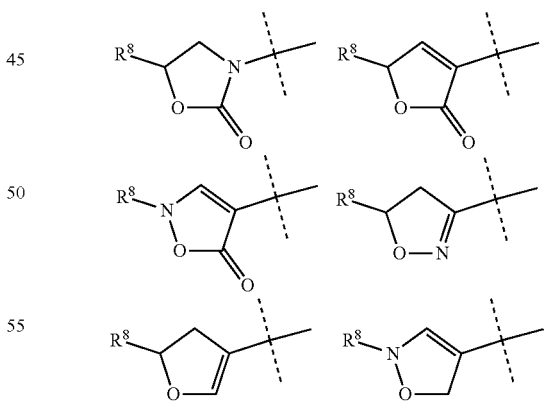

$R^6$ is H, F, Cl or OMe;
$R^7$ is H, F, Cl, OH, $NH_2$, a substituted or unsubstituted alkyl group or a substituted or unsubstituted heteroalkyl group, or
$R^3$ and $R^7$ can be linked via an alkylene, an alkenylene or a heteroalkylene group or be a part of a cycloalkylene or heterocycloalkylene group; in case $R^3$ is no H and $R^7$ is no H, F, OH, $NH_2$ or Cl; and $R^8$ is a $C_{1-6}$ alkyl, a $C_{1-6}$ heteroalkyl or a heteroaralkyl group, all of which may optionally be substituted;

or a pharmacologically acceptable salt, solvate, hydrate or formulation thereof.

The term alkyl refers to a saturated straight or branched chain hydrocarbon group, preferably containing from one to ten, especially preferably from one to six carbon atoms, for example methyl, ethyl, propyl, isopropyl, butyl, iso-butyl, sec-butyl, tert-butyl, n-pentyl, iso-pentyl, n-hexyl, 2,2-dimethylbutyl, n-octyl or n-pentyl groups. Any alkyl group as defined herein may be substituted with one, two or more substituents, for example F, Cl, Br, I, $NH_2$, OH, SH or $NO_2$.

The terms alkenyl and alkynyl refer to an unsaturated straight or branched chain hydrocarbon group (having one, two or more double and/or triple bonds, an alkenyl preferably having one or two double bonds and an alkynyl preferably having one or two triple bonds), preferably containing two to ten, preferably two to six carbon atoms for example: ethenyl (vinyl), propenyl (allyl), iso-propenyl, n-pentenyl, butenyl, isoprenyl or hexa-2-enyl; ethynyl, propynyl or butynyl groups. Any alkenyl or alkynyl group as defined herein may be substituted with one, two or more substituents, for example F, Cl, Br, I, $NH_2$, OH, SH or $NO_2$.

The term heteroalkyl refers to an alkyl, alkenyl or alkynyl group as defined herein wherein one or more carbon atoms are replaced by an oxygen, nitrogen, phosphorous or sulphur atom or by a SO group or by a $SO_2$ group, for example an alkoxy group such as methoxy, ethoxy, propoxy, isopropoxy, butoxy or tert.-butoxy, an alkoxyalkyl group such as methoxymethyl, ethoxymethyl, 1-methoxyethyl, 1-ethoxyethyl, 2-methoxyethyl or 2-ethoxyethyl, an alkylamino group such as methylamino, ethylamino, propylamino, isopropylamino, dimethylamino or diethylamino, an alkylthio group such as methylthio, ethylthio or isopropylthio or a cyano group. It may also refer to one of the above groups containing a keto group. The term heteroalkyl furthermore refers to a group derived from a carboxylic acid or carboxylic acid amide such as acetyl, propionyl, acetyloxy, propionyloxy, acetylamino or propionylamino, a carboxyalkyl group such as carboxymethyl, carboxyethyl or carboxypropyl, a carboxyalkyl ester, an alkylthiocarboxyamino group, an alkoxyimino group, an alkylaminothiocarboxyamino group or an alkoxycarbonylamino group. Any heteroalkyl group as defined herein may be substituted with one, two or more substituents, for example F, Cl, Br, I, $NH_2$, OH, SH or $NO_2$.

The term $C_1$-$C_6$ heteroalkyl refers to a heteroalkyl group containing from 1 to 6 carbon atoms and 1, 2 or 3 heteroatoms selected from 0, S and/or N (especially 0 and/or N).

The term cycloalkyl refers to a saturated or partially unsaturated (having one, two or more double and/or triple bonds) cyclic group with one, two or more rings, having three to 14 carbon ring-atoms, preferably from five or six to ten carbon ring-atoms, for example cyclopropyl, cyclobutyl, cyclopentyl, cyclohexyl, tetralin, cyclopentenyl or cyclohex-2-enyl groups. Any cycloalkyl group as defined herein may be substituted with one, two or more substituents, for example F, Cl, Br, I, OH, =O, $NH_2$, =NH, SH, =S, $N_3$, $NO_2$, alkyl groups such as methyl or ethyl, heteroalkyl groups such as methoxy, methylamino, dimethylamino or cyanide.

The term heterocycloalkyl refers to a cycloalkyl group as defined herein where one, two or more carbon ring-atoms are replaced by one, two or more oxygen, nitrogen, phosphorous or sulphur atoms or $S(O)_{1-2}$ groups for example piperidino, morpholino or piperazino groups.

The term alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two rings having from 3 to 10 (especially 3, 4, 5, 6 or 7) ring carbon atoms, and one or two alkyl, alkenyl or alkynyl groups (especially alkyl groups) having 1 or 2 to 6 carbon atoms.

The term heteroalkylcycloalkyl refers to alkylcycloalkyl groups as defined above in which one or more (preferably 1, 2 or 3) carbon atoms have been replaced by an oxygen, nitrogen, phosphorus or sulfur atom (preferably by an oxygen, sulfur or nitrogen atom) or a SO group or a $SO_2$ group. A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to carbon atoms. Examples of such groups are alkylheterocycloalkyl, alkylheterocycloalkenyl, alkenylheterocycloalkyl, alkynylheterocycloalkyl, heteroalkylcycloalkyl, heteroalkyl-heterocycloalkyl and heteroalkylheterocycloalkenyl, the cyclic groups being saturated or mono-, di- or tri-unsaturated.

The term aryl refers to an aromatic cyclic group with one, two or more rings, having five to 14 carbon ring-atoms preferably from five or six to ten carbon ring-atoms, for example phenyl or naphthyl groups. Any aryl group as defined herein may be substituted with one, two or more substituents, for example F, Cl, Br, I, OH, $NH_2$, SH, $N_3$, $NO_2$, alkyl groups such as methyl or ethyl, heteroalkyl groups such as methoxy, methylamino, dimethylamino or cyanide.

The term heteroaryl refers to an aromatic group that contains one or more rings containing from 5 to 14 ring atoms, preferably from 5 to 10 (especially 5 or 6 or 9 or 10) ring atoms, and contains one or more (preferably 1, 2, 3 or 4) oxygen, nitrogen, phosphorus or sulfur ring atoms (preferably 0, S or N) in addition to the carbon ring atoms. The expression heteroaryl refers furthermore to groups that are substituted by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The term aralkyl (or arylalkyl or alkylaryl) refers to groups that comprise both, aryl as well as alkyl, alkenyl, alkynyl and/or cycloalkyl groups.

The term heteroaralkyl (or heteroarylalkyl or heteroalkylaryl or heteroalkylheteroaryl etc.) refers to an aralkyl group as defined herein where one, two, three or more carbon atoms are replaced by one, two, three or more oxygen, nitrogen, phosphorous or sulphur atoms or $S(O)_{1-2}$ groups, that is to say to groups containing both aryl or heteroaryl, respectively, and also alkyl, alkenyl, alkynyl and/or heteroalkyl and/or cycloalkyl and/or heterocycloalkyl groups in accordance with the above definitions.

Preferably, any alkyl, alkenyl, alkynyl, heteroalkyl, cycloalkyl, heterocycloalkyl, alkylcycloalkyl, heteroalkylcycloalkyl, aryl, heteroaryl, aralkyl or heteroarylalkyl groups as defined herein may be substituted with one or more halogen atoms, NH$_2$, SH, NO$_2$ or OH groups or unsubstituted alkyl, heteroalkyl, aryl, aralkyl, aralkyloxy, heteroaryl, cycloalkyl or heterocycloalkyl groups as defined herein.

The term "optionally substituted" or "substituted" refer to groups wherein one or more hydrogen atoms may be replaced by a halogen atom, a NH$_2$, SH, =NH, =S, =O, NO$_2$ or OH group or by an unsubstituted alkyl, heteroalkyl, aryl, aralkyl, aralkyloxy, heteroaryl, cycloalkyl or heterocycloalkyl group as defined herein. Preferred substituents are F, Cl, OH and NH$_2$.

In the context of the present invention, the terms antibacterial agent(s), antibacterial(s), antimicrobial(s), antimicrobial agent(s) and antibacterial compound(s) preferably have the same meaning. Further, in the context of the present invention the term oxazolidinone-quinolone hybrid preferably refers to oxazolidinone-quinolone hybrid antibacterials.

Preferred and/or advantageous embodiments of the invention are subject-matter of the subclaims.

Preferred are compounds of Formula (I), wherein R$^1$ is H.

Further preferred are compounds of Formula (I), wherein R$^2$ is F or H.

Moreover preferred are compounds of Formula (I), wherein R$^3$ is an ethyl, a 2-propyl, a C$_3$-C$_6$ cycloalkyl (i.e. cyclopropyl, cyclobutyl, cyclopentyl or cyclohexyl), a phenyl or a pyridyl group. All these groups may be substituted with one, two, three or more fluorine atoms or amino groups.

Moreover preferred are compounds of Formula (I), wherein R$^3$ is a cyclopropyl group.

Further preferred are compounds of Formula (I), wherein R$^7$ and R$^3$ together form a bridge of the formula —O—CH$_2$—N(Me)- or —O—CH$_2$—CH(Me)- wherein the oxygen atom is bound to position X. Herein, the preferred stereochemistry at the chiral center is the one giving the (S) configuration in the final compound.

Moreover preferred are compounds of formula (I), wherein R$^4$ is a hydrogen atom or a group of formula SO$_3$H, PO$_3$H$_2$, CH$_2$OPO$_3$H$_2$ or COCH$_2$CH$_2$COOH.

Further preferred are compounds of formula (I), wherein R$^4$ is an ester of a naturally occurring amino acid or a derivative thereof (preferably a group of formula —CO-CHR'NH$_2$ or a derivative like an ester, amide or alkylamine thereof, wherein R' is the side chain of a naturally occurring amino acid like aspartic acid, glutaric acid, lysine, etc; e.g. dimethyl aminoglycine OCOCH$_2$N(CH$_3$)$_2$).

Especially preferred are compounds of formula (I), wherein R$^4$ is a hydrogen atom or a group of formula PO$_3$H$_2$.

Most preferred are compounds of formula (I), (II) or (III), wherein R$^4$ is a group of formula PO$_3$H$_2$ or salts thereof (especially a sodium salt).

Further preferred are compounds of Formula (I), wherein R$^5$ has the following structure:

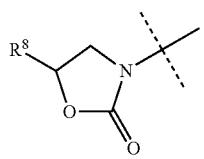

Moreover preferred are compounds of Formula (I), wherein R$^5$ has the following structure:

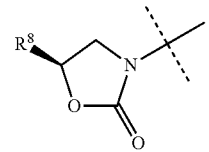

Further preferred are compounds of Formula (I), wherein R$^8$ is a C$_{1-6}$ alkyl or a C$_{1-6}$ heteroalkyl group.

Moreover preferred are compounds of Formula (I), wherein R$^8$ is a group of the formula —CH$_2$NHCOCH=CHAryl, —CH$_2$OHeteroaryl (especially -oxa-3-oxazol), —CH$_2$NHSO$_2$Me, —CH$_2$NHCOOMe, —CH$_2$NHCOMe, —CH$_2$NHCS$_2$Me, —CH$_2$NHCSMe, —CH$_2$NHCSNH$_2$, —CH$_2$NHCSOMe or —NHCOMe; especially —CH$_2$NHCSMe, —CH$_2$OH or —CH$_2$NHCOMe.

Especially preferred are compounds of Formula (I), wherein R$^8$ is a group of the formula —CH$_2$NHCOMe or —CH$_2$OH.

Further especially preferred are compounds of Formula (I), wherein R$^5$ has the following structure:

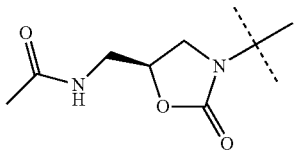

Moreover especially preferred are compounds of Formula (I), wherein R$^5$ has the following structure:

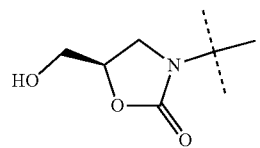

Moreover preferred are compounds of Formula (I), wherein R$^7$ is H, F, Cl or a methoxy group that may be substituted by one, two or three fluorine atoms.

Especially preferred are compounds of Formula (I), wherein R$^7$ is H or a methoxy group.

Further preferred are compounds of formula (I), wherein X is N or CH; especially preferably, X is CH.

Moreover preferred are compounds of Formula (I), wherein Y is CH.

Further preferred are compounds of formula (I), wherein n is 1 or 2; especially preferably 2.

Moreover preferred are compounds of Formula (I), wherein m is 2.

Further preferred are compounds of Formula (I), wherein A is C$_{1-6}$ alkylene, C$_{2-6}$ alkenylene, C$_{2-6}$ alkynylene, C$_{1-6}$ heteroalkylene, cyclopropylene, epoxide, aziridine, thioepoxide, lactame or lactone, all of which groups may be substituted.

Especially preferred are compounds of formula (I), wherein A is a group of formula —CH$_2$CH$_2$—, —OCH$_2$—, —OCH$_2$CH$_2$—, —SCH$_2$—, —SCH$_2$CH$_2$—, —CH=CH—, —C≡C—, —CH(OH)CH(OH)— or —CH(NH₂)CH(OH)—. Especially preferably, A is a group of formula —OCH₂—, wherein the oxygen atom is bound to the aromatic ring comprising group Y.

Moreover preferred are compounds of formula (I), wherein A is a group of Formula —O—B—, wherein B is a $C_{1-4}$ alkylene group, a $C_{2-4}$ alkenylene group, a $C_{2-4}$ alkynylene group or a $C_{1-4}$ heteroalkylene group, all of which groups may be substituted by one, two or more hydroxy or amino groups. Therein, the oxygen atom is bound to the aromatic ring comprising Y and B is bound to the heterocycloalkyl group at the carbon atom carrying group —O—R⁴.

Especially preferred are compounds of formula (I), wherein B is $CH_2$ or $CH_2CH_2$; especially preferably $CH_2$.

Especially preferred the oxazolidinone-quinolone hybrid is a compound of formula (II)

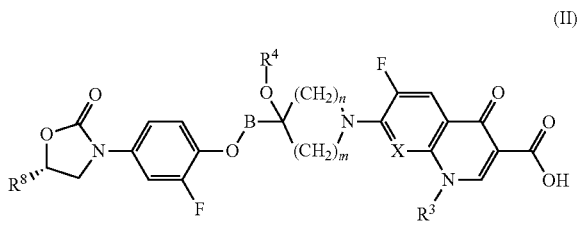

(II)

wherein R³, R⁴, R⁸, X, B, n and m are defined as above or a pharmacologically acceptable salt, solvate, hydrate or formulation thereof.

In a preferred embodiment B is $CH_2$; X is CH, N or C—OMe and R³ is cyclopropyl or X is CR⁷ and R⁷ and R³ together form a bridge of the formula —O—CH₂—CH(Me)-, wherein the preferred stereochemistry at the chiral center is the one giving the (S) configuration in the final compound, n is 1, 2 or 3 (especially 1 or 2), m is 1, 2 or 3 (especially 2), R⁴ is a hydrogen atom or a group of formula PO₃H₂ and R⁸ is a group of the formula —CH₂NHCOMe or —CH₂OH or a pharmacologically acceptable salt, solvate, hydrate or formulation thereof.

Further preferred the oxazolidinone-quinolone hybrid is a compound of formula (III):

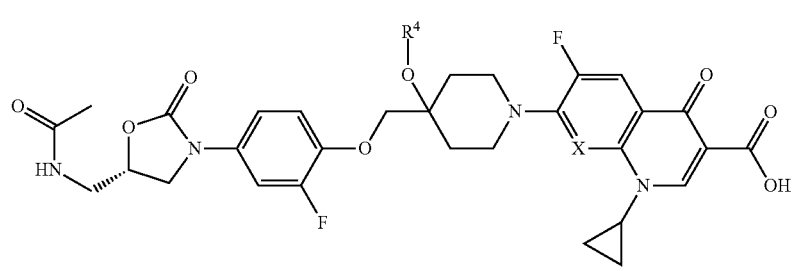

(III)

wherein X is N or CH (especially preferably CH) and R⁴ is a hydrogen atom or a group of formula PO₃H₂ or a pharmacologically acceptable salt, solvate, hydrate or formulation thereof.

Moreover preferred are the mono, di or tri sodium salts (most preferred the mono sodium salts) of compounds of formula (I), (II) or (III) or mixtures thereof, especially, when R⁴ is PO₃H₂. Especially preferred are the mono, di or tri sodium salts (most preferred the mono sodium salts) of compounds of formula (I), (II) or (III), wherein R⁴ is PO₃H₂ or mixtures thereof.

Especially preferred the oxazolidinone-quinolone hybrid is selected from the following compounds:
7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-[1,8]naphthyridine-3-carboxylic acid;
7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-[1,8]naphthyridine-3-carboxylic acid;
7-[4-{4-[(5S)-5-(Acetylamino-methyl)-2-oxo-oxazolidin-3-yl]-2-fluoro-phenoxymethyl}-4-(2,6-diamino-hexanoyloxy)-piperidin-1-yl]-1-cyclopropyl-6-fluoro-4-oxo-1,4-dihydro-[1,8]naphthyridine-3-carboxylic acid;
Succinic acid mono-[4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl] ester;
7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid;
7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid;
7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-8-methoxy-4-oxo-1,4-dihydro-quinoline-3-carboxylic acid;
7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-8-methoxy-4-oxo-1,4-dihydro-quinoline-3-carboxylic acid;
9-(4-{4-[(5S)-5-(Acetylamino-methyl)-2-oxo-oxazolidin-3-yl]-2-fluoro-phenoxymethyl}-4-hydroxy-piperidin-1-yl)-8-fluoro-3-methyl-6-oxo-2,3-dihydro-6H-1-oxa-3a-azaphenalene-5-carboxylic acid;
7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-[1,8]naphthyridine-3-carboxylic acid;
7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-quinoline-3-carboxylic acid;
7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-8-methoxy-4-dihydro-quinoline-3-carboxylic acid;
7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-8-methoxy-4-oxo-1,4-dihydro-quinoline-3-carboxylic acid;
9-(3-{4-[(5S)-5-(Acetylamino-methyl)-2-oxo-oxazolidin-3-yl]-2-fluoro-phenoxymethyl}-3-hydroxy-pyrrolidin-1- yl)-8-fluoro-3-methyl-6-oxo-2,3-dihydro-6H-1-oxa-3a-aza-phenalene-5-carboxylic acid;

7-(4-{4-[(5S)-5-(Acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-quinoline-3-carboxylic acid;

7-(4-{4-[(5S)-5-(Acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-[1,8]naphthyridine-3-carboxylic acid;

7-(4-{4-[5S-(acetylamino-methyl)-2-oxo-oxazolidin-3-yl]-2-fluoro-phenylethynyl}-4-hydroxy-piperidin-1-yl)-1-cyclopropyl-6-fluoro-4-oxo-1,4-dihydro-quinoline-3-carboxylic acid;

7-(4-{4-[S5-(acetylamino-methyl)-2-oxo-oxazolidin-3-yl]-2-fluoro-phenylethynyl}-4-hydroxy-piperidin-1-yl)-1-cyclopropyl-6-fluoro-4-oxo-1,4-dihydro-[1,8]-napthyridine-3-carboxylic acid;

7-[4-(2-{4-[5S-(acetylamino-methyl)-2-oxo-oxazolidin-3-yl]-2-fluoro-phenyl}-ethyl)-4-hydroxy-piperidin-1-yl]-1-cyclopropyl-6-fluoro-4-oxo-1,4-dihydro-quinoline-3-carboxylic acid;

1-cyclopropyl-6-fluoro-7-[4-({2-fluoro-4-[(5R)-5-(hydroxymethyl)-2-oxo-1,3-oxazolidin-3-yl]phenoxy}methyl)-4-hydroxypiperidin-1-yl]-4-oxo-1,4-dihydroquinolin-3-carboxylic acid;

or a pharmacologically acceptable salt, solvate, hydrate or formulation thereof.

Further especially preferred is the sodium salt of 7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid or a pharmacologically acceptable solvate, hydrate or formulation thereof.

More preferably the oxazolidinone-quinolone hybrid is selected from the following compounds:

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid:

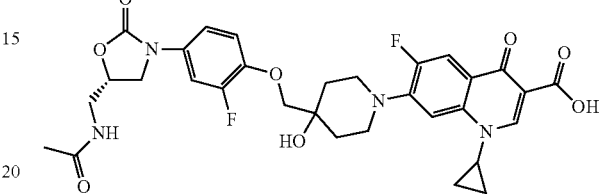

and 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

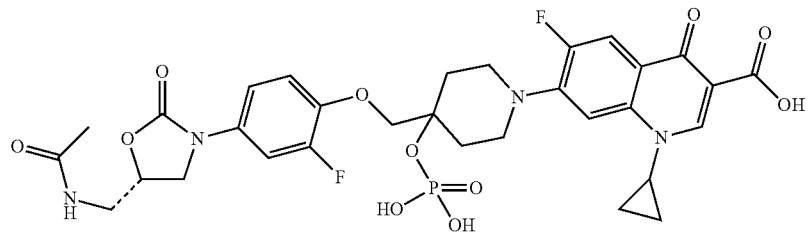 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

or a salt thereof, such as e.g.: the sodium salt of 7-(4-{4-[(S5)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

Most preferably, the oxazolidinone-quinolone hybrid is the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

According to an especially preferred embodiment, the present invention provides a method for administering an oxazolidinone-quinolone hybrid, comprising administering to a patient in need thereof the oxazolidinone-quinolone hybrid at an infusion rate of from 0.4 to 3.0 (preferably from 0.4 to 1.5; especially preferably from 0.4 to 0.75) mg/(kg body weight×h), wherein the oxazolidinone-quinolone hybrid is:

7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

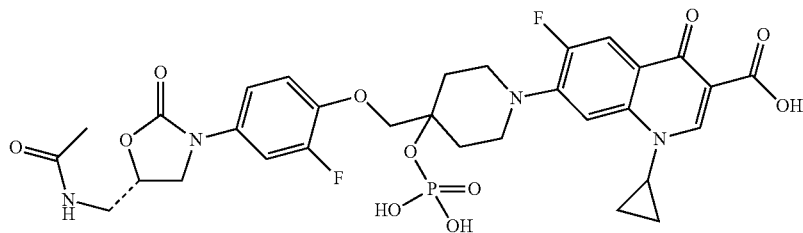 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

or a salt thereof, such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

According to a further especially preferred embodiment, the present invention provides a method for the use of an oxazolidinone-quinolone hybrid for the manufacture of a medicament for treating a bacterial infection in a patient in need thereof wherein the oxazolidinone-quinolone hybrid is administered at an infusion rate of from 0.4 to 3.0 (preferably from 0.4 to 1.5; especially preferably from 0.4 to 0.75) mg/(kg body weight×h), wherein the oxazolidinone-quinolone hybrid is:

7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

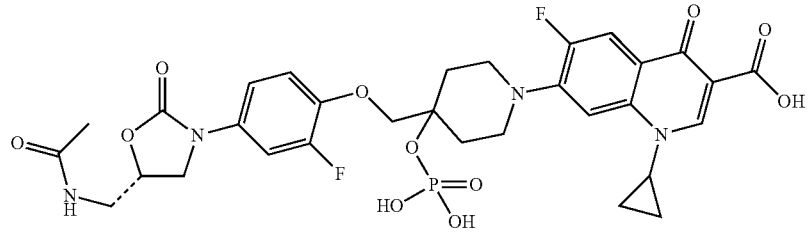 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

or a salt thereof, such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

According to a further especially preferred embodiment, the present invention provides an oxazolidinone-quinolone hybrid for use in the treatment of a bacterial infection, said treatment comprising the administration of the oxazolidinone-quinolone hybrid at an infusion rate of from 0.4 to 3 (preferably from 0.4 to 1.5; especially preferably from 0.4 to 0.75) mg/(kg body weight×h), wherein the oxazolidinone-quinolone hybrid is:

7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

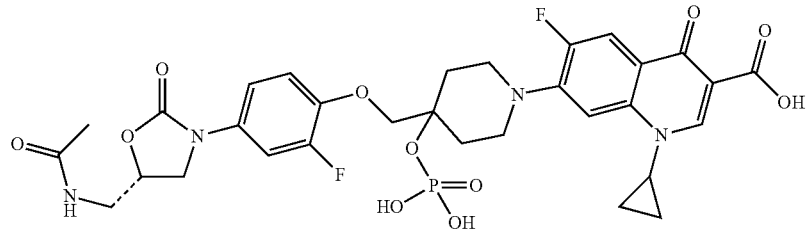 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

or a salt thereof, such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

According to the present invention an infusion rate from 0.4 to 0.75 mg/(kg BW×h) is especially preferred.

The infusion rates of the present invention may be used for patients in clinical applications and in veterinary applications. The infusion rates (mg/(kg BW×h)) of the oxazolidinone-quinolone hybrids of the present invention are safe and efficacious in clinical or veterinary applications.

In an especially preferred embodiment, the infusion rate of the present invention is 0.5 mg/(kg BW×h).

Moreover especially preferred is the administration of the sodium salt of 7-(4-{4-[(S5)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid at a dose of 6 mg/kg body weight over 12 hours for 5 consecutive days to humans.

The methods of the instant invention may also be practiced while concurrently administering one or more antibiotics other than an oxazolidinone-quinolone hybrid antibacterial.

The methods of the present invention are especially useful for the treatment of bacterial infections caused by gram-positive bacteria.

According to a further embodiment, the present invention provides compounds of formula (I),

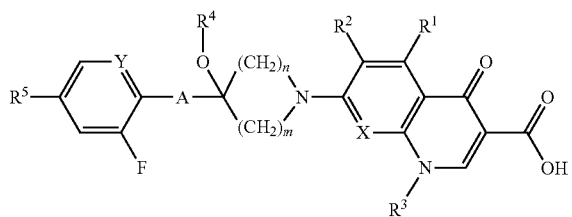

(I)

wherein

A is an alkylene group, an alkenylene group, an alkynylene group, a heteroalkylene group, a cycloalkylene group, a heterocycloalkylene group, an arylene group or a heteroarylene group all of which groups may be substituted;

X is CR$^7$ or N;
Y is CR$^6$ or N;
n is 1, 2 or 3;
m is 1, 2 or 3;
R$^1$ is H, F, Cl, Br, I, OH, NH$_2$, an alkyl group or a heteroalkyl group;
R$^2$ is H, F or Cl;
R$^3$ is H, an alkyl group, an alkenyl group, an alkynyl group, a heteroalkyl group, a cycloalkyl group, a heterocycloalkyl group, an alkylcycloalkyl group, a heteroalkylcycloalkyl group, an aryl group, a heteroaryl group, an alkylaryl group or a heteroarylalkyl group; all of which groups may be substituted with one, two or more halogen atoms like F or Cl or amino groups.
R$^4$ is a hydrogen atom, a group of formula PO$_3$R$^9{}_2$ or SO$_3$R$^{10}$ or a heteroalkyl group carrying at least one OH, NH$_2$, SO$_3$R$^{10}$, PO$_3$R$^9{}_2$ or COOH group or an ester of a naturally occurring amino acid or a derivative thereof, wherein the groups R$^9$ independently of each other are H, alkyl, cycloalkyl, aryl or aralkyl and wherein R$^{10}$ is H, alkyl, cycloalkyl, aryl or aralkyl;

R$^5$ is selected from following groups:

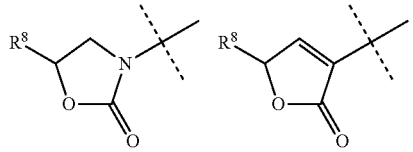

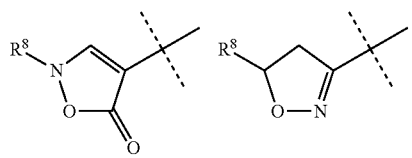

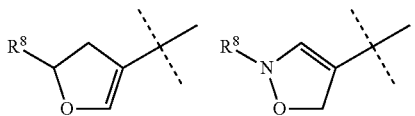

R$^6$ is H, F, Cl or OMe;
R$^7$ is H, F, Cl, OH, NH$_2$, a substituted or unsubstituted alkyl group or a substituted or unsubstituted heteroalkyl group, or
R$^3$ and R$^7$ can be linked via an alkylene, an alkenylene or a heteroalkylene group or be a part of a cycloalkylene or heterocycloalkylene group; in case R$^3$ is no H and R' is no H, F, OH, NH$_2$ or Cl; and
R$^8$ is a C$_{1-6}$ alkyl, a C$_{1-6}$ heteroalkyl, a heteroarylalkyl, a heteroalkylaryl or a heteroalkylheteroaryl group, all of which may optionally be substituted;

or a pharmacologically acceptable salt, solvate, hydrate or formulation thereof, for use in the parenteral (especially intravenous) treatment or prophylaxis of bacterial diseases.

Especially preferred are compounds of formula (II)

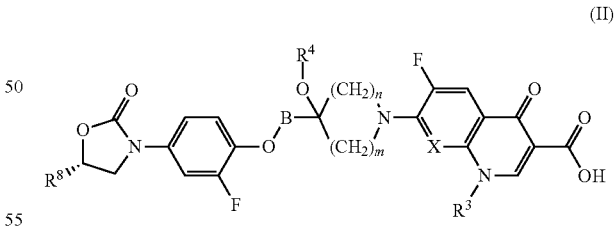

(II)

wherein R$^3$, R$^4$, R$^8$, X, B, n and m are defined as above or a pharmacologically acceptable salt, solvate, hydrate or formulation thereof, for use in the parenteral (especially intravenous) treatment or prophylaxis of bacterial diseases.

In a preferred embodiment B is CH$_2$; X is CH, N or C—OMe and R$^3$ is cyclopropyl or X is CR$^7$ and R$^7$ and R$^3$ together form a bridge of the formula —O—CH$_2$—CH (Me)-, wherein the preferred stereochemistry at the chiral center is the one giving the (S) configuration in the final compound, n is 1, 2 or 3 (especially 1 or 2), m is 1, 2 or 3 (especially 2), R$^4$ is a hydrogen atom or a group of formula PO$_3$H$_2$ and R$^8$ is a group of the formula —CH$_2$NHCOMe or —CH$_2$OH or a pharmacologically acceptable salt, solvate, hydrate or formulation thereof.

Further preferred are compounds of formula (III):

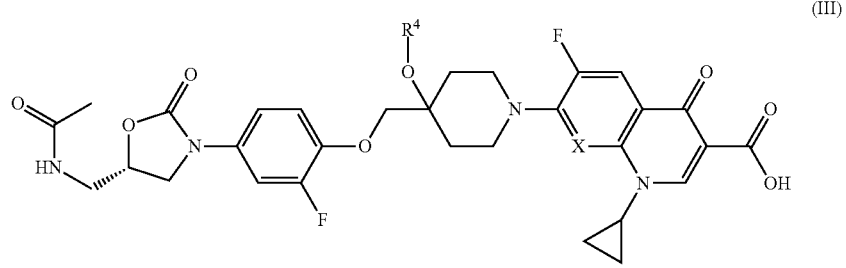

(III)

wherein X is N or CH (especially preferably CH) and R$^4$ is a hydrogen atom or a group of formula PO$_3$H$_2$ or a pharmacologically acceptable salt, solvate, hydrate or formulation thereof, for use in the parenteral (especially intravenous) treatment or prophylaxis of bacterial diseases.

Moreover preferred are the mono, di or tri sodium salts (most preferred the mono sodium salts) of compounds of formula (I), (II) or (III) or mixtures thereof. Especially preferred are the mono, di or tri sodium salts (most preferred the mono sodium salts) of compounds of formula (I), (II) or (III), wherein R$^4$ is PO$_3$H$_2$ or mixtures thereof, for use in the parenteral (especially intravenous) treatment or prophylaxis of bacterial diseases.

Especially preferred are the following compounds:

7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-[1,8]naphthyridine-3-carboxylic acid;

7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-[1,8]naphthyridine-3-carboxylic acid;

7-[4-{4-[(5S)-5-(Acetylamino-methyl)-2-oxo-oxazolidin-3-yl]-2-fluoro-phenoxymethyl}-4-(2,6-diamino-hexanoyloxy)-piperidin-1-yl]-1-cyclopropyl-6-fluoro-4-oxo-1,4-dihydro-[1,8]naphthyridine-3-carboxylic acid;

Succinic acid mono-[4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl] ester;

7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid;

7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid;

7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-8-methoxy-4-oxo-1,4-dihydro-quinoline-3-carboxylic acid;

7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-8-methoxy-4-oxo-1,4-dihydro-quinoline-3-carboxylic acid;

9-(4-{4-[(5S)-5-(Acetylamino-methyl)-2-oxo-oxazolidin-3-yl]-2-fluoro-phenoxymethyl}-4-hydroxy-piperidin-1-yl)-8-fluoro-3-methyl-6-oxo-2,3-dihydro-6H-1-oxa-3a-aza-phenalene-5-carboxylic acid;

7-(3-{4-[(S5)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-[1,8]naphthyridine-3-carboxylic acid;

7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-quinoline-3-carboxylic acid;

7-(3-{4-[(S5)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-8-methoxy-4-oxo-1,4-dihydro-quinoline-3-carboxylic acid;

7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-8-methoxy-4-oxo-1,4-dihydro-quinoline-3-carboxylic acid;

9-(3-{4-[(S5)-5-(Acetylamino-methyl)-2-oxo-oxazolidin-3-yl]-2-fluoro-phenoxymethyl}-3-hydroxy-pyrrolidin-1-yl)-8-fluoro-3-methyl-6-oxo-2,3-dihydro-6H-1-oxa-3a-aza-phenalene-5-carboxylic acid;

7-(4-{4-[(5S)-5-(Acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-quinoline-3-carboxylic acid;

7-(4-{4-[(5S)-5-(Acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-[1,8]naphthyridine-3-carboxylic acid;

7-(4-{4-[5S-(acetylamino-methyl)-2-oxo-oxazolidin-3-yl]-2-fluoro-phenylethynyl}-4-hydroxy-piperidin-1-yl)-1-cyclopropyl-6-fluoro-4-oxo-1,4-dihydro-quinoline-3-carboxylic acid;

7-(4-{4-[5S-(acetylamino-methyl)-2-oxo-oxazolidin-3-yl]-2-fluoro-phenylethynyl}-4-hydroxy-piperidin-1-yl)-1-cyclopropyl-6-fluoro-4-oxo-1,4-dihydro-[1,8]-napthyridine-3-carboxylic acid;

7-[4-(2-{4-[5S-(acetylamino-methyl)-2-oxo-oxazolidin-3-yl]-2-fluoro-phenyl}-ethyl)-4-hydroxy-piperidin-1-yl]-1-cyclopropyl-6-fluoro-4-oxo-1,4-dihydro-quinoline-3-carboxylic acid;

1-cyclopropyl-6-fluoro-7-[4-({2-fluoro-4-[(5R)-5-(hydroxymethyl)-2-oxo-1,3-oxazolidin-3-yl]phenoxy}methyl)-4-hydroxypiperidin-1-yl]-4-oxo-1,4-dihydroquinolin-3-carboxylic acid;

or a pharmacologically acceptable salt, solvate, hydrate or formulation thereof, for use in the parenteral (especially intravenous) treatment or prophylaxis of bacterial diseases.

Further especially preferred is the sodium salt of 7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid or a pharmacologically acceptable solvate, hydrate or formulation thereof, for use in the parenteral (especially intravenous) treatment or prophylaxis of bacterial diseases.

Most preferably are the following compounds:
7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid:

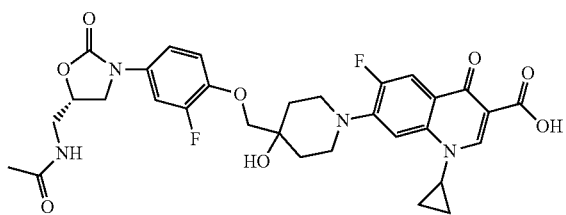 [SMILES: CC(=O)NC[C@H]1CN(c2ccc(OCC3(O)CCN(c4cc5c(cc4F)c(=O)c(C(=O)O)cn5C4CC4)CC3)c(F)c2)C(=O)O1]

and
7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

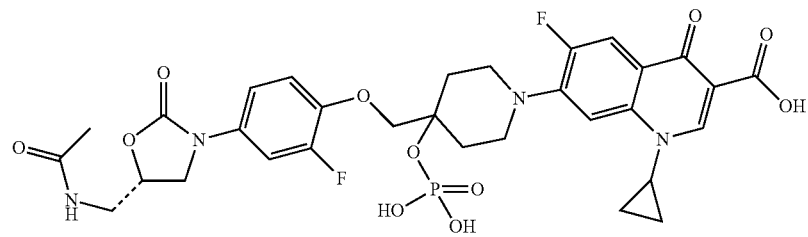

or a salt thereof, such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid, for use in the parenteral (especially intravenous) treatment or prophylaxis of bacterial diseases.

The pharmaceutical compositions of the present invention contain an oxazolidinone-quinolone hybrid (e.g. a compound of Formula (I), (II) or (III)) as the active agent and optionally carriers and/or diluents and/or adjuvants. Optionally the pharmaceutical compositions according to the present invention may also contain additional known antibiotics.

The compounds and pharmaceutical compositions disclosed herein can be used for the parenteral (especially intravenous) treatment or prophylaxis of bacterial diseases, especially for the parenteral (especially intravenous) treatment or prophylaxis of intestinal diseases which are caused by Gram-positive bacteria (e.g. *S. aureus, Enterococcus* spp.), especially Gram-positive anaerobes such as *Clostridium* spp., in particular *Clostridium difficile, Clostridium perfringens* (especially by *Clostridium difficile*).

It is a further object of the present invention to provide compounds of formula (I), (II) or (III) as defined herein or a pharmaceutical composition as defined herein for the preparation of a medicament for the parenteral (especially intravenous) treatment or prophylaxis of bacterial diseases, especially for the parenteral (especially intravenous) treatment or prophylaxis of intestinal diseases which are caused by Gram-positive bacteria (e.g. *S. aureus, Enterococcus* spp.), especially Gram-positive anaerobes such as *Clostridium* spp., in particular *Clostridium difficile, Clostridium perfringens* (especially by *Clostridium difficile*).

It is moreover an object of the present invention to provide a method for the treatment or prophylaxis of bacterial diseases (especially for the parenteral (especially intravenous) treatment or prophylaxis of intestinal diseases which are caused by Gram-positive bacteria (e.g. *S. aureus, Enterococcus* spp.), especially Gram-positive anaerobes such as *Clostridium* spp., in particular *Clostridium difficile, Clostridium perfringens* (especially by *Clostridium difficile*)) comprising the parenteral (especially intravenous) administration, to a patient in need thereof, of a therapeutically effective amount of a compound or a pharmaceutical composition described herein.

The intestinal diseases intended to be prevented or treated according to the present invention comprise e.g. diarrhea, colitis and pseudomembranous colitis. Said intestinal diseases can e.g. be caused by *Clostridium difficile* (and especially by a toxin producing strain of *Clostridium difficile*).

Especially preferably, the compounds and pharmaceutical compositions disclosed herein can be used for the parenteral (especially intravenous) treatment or prophylaxis of severe or complicated cases of bacterial diseases (especially *Clostridium difficile* associated diseases) such as ileus, toxic megacolon, fulminant colitis, colonic perforation or need for colectomy.

Moreover especially preferably, the compounds and pharmaceutical compositions disclosed herein can be used for the parenteral (especially intravenous) treatment or prophylaxis of recurrent cases of bacterial diseases (especially *Clostridium difficile* associated diseases such as *Clostridium difficile* associated diarrhea).

The present invention also relates to pharmacologically acceptable salts, or solvates and hydrates, respectively, and to compositions and formulations of compounds of Formula (I), (II) or (III). Moreover, the present invention also relates to the use of pharmacologically acceptable salts, or solvates and hydrates, respectively, and to compositions and formulations of oxazolidinone-quinolone hybrids (e.g. compounds of Formula (I), (II) or (III)).

Examples of pharmacologically acceptable salts of sufficiently basic compounds of Formula (I), (II) or (III) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicyclic acid. Further, a sufficiently acidic compound of Formula (I), (II) or (III) may form alkali or earth alkaline metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts.

Compounds of Formula (I), (II) or (III) may be solvated, especially hydrated. The hydratisation can occur during the process of production or as a consequence of the hygroscopic nature of the initially water free compounds of Formula (I), (II) or (III).

It should be appreciated that certain compounds of formula (I), (II) or (III) as mentioned in this description may have tautomeric forms from which only one might be specifically mentioned or depicted in this description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). Further, some compounds may display polymorphism. All these tautomeric forms, geometrical or optical isomers (as well as racemates and diastereomers) and polymorphous forms are included in the invention. The compounds of Formula (I), (II) or (III) may further be present either as achiral compounds, mixtures of diastereomers, mixtures of enantiomers or as optically pure compounds.

As mentioned above, therapeutically useful agents that contain compounds of Formula (I), (II) or (III), their solvates, salts or formulations are also comprised in the scope of the present invention.

According to the invention, the oxazolidinone-quinolone hybrids (e.g. compounds of Formula (I), (II) or (III)) will be administered parenterally including intravenous, intramuscular and subcutaneous injection, e.g. as an injectable solution or suspension. Preferably, the oxazolidinone-quinolone hybrids (e.g. compounds of Formula (I), (II) or (III)) will be administered intravenously.

For the production of liquid solutions, emulsions or suspensions one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4).

When intravenously administered to several animal species, among them mice and rats, the sodium salt of 7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid (Compound 1) was rapidly converted to the active substance 7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid (Compound 2). The very good solubility in aqueous media allows for (Compound 1) to be easily formulated, using lyophilisation. To improve stability and to reduce reconstitution time of the lyophilisate, Compound 1 can e.g. be formulated together with sorbitol and sodium hydroxide and lyophilised in glass vials. The lyophilisate can be easily reconstituted by addition of water for injection and gentle shaking to form a yellow, sterile solution ready for intravenous injection.

The pharmaceutical compositions of the present invention may also contain additives for conservation and/or stabilisation, e.g. UV stabilizers, emulsifiers, salts to change the osmotic pressure, buffers and antioxidants.

Compounds of formula (I), (II) and (III) can be synthesized according to procedures described in the prior art (e.g. in WO 02/059116, WO 03/002560, WO 03/031443, WO 03/032962, WO 2004/096221, WO 2005/058888, WO 2008/056335 and WO 2009/136379). The antibacterial activity of these compounds is described in these documents and further e.g. in U.S. Pat. Nos. 8,329,908 and 8,513,231 and documents cited therein.

For example, Compound 2 shows the following activities against several bacterial strains. MIC testing was done according to CLSI (formerly NCCLS) guidelines: Performance Standards for Antimicrobial Susceptibility Testing 11$^{th}$ Informational Supplement, Vol. 21 No 1, M100-S11, January 2001. NCCLS. Revised edition: 17$^{th}$ Informational Supplement, Vol. 27 No 1, M100-S16, January 2007.

| Bacterial strains | MIC (mg/l) |
| --- | --- |
| Staphylococcus aureus ATCC 29213 | 0.5 |
| Staphylococcus aureus ATCC 33593 | 0.25 |
| Staphylococcus aureus ATCC 43300 | 0.5 |
| Staphylococcus aureus Visa Mu 50 | 0.5 |
| Staphylococcus aureus NRS 120 | 2 |
| Streptococcus pneumoniae ATCC 33400 | 0.03 |
| Enterococcus faecalis ATCC 29212 | 0.25 |
| Enterococcus faecalis ATCC 51299 | 0.25 |

EXAMPLES

Example 1 (Infusion Rate)

Compound 1 has been administered to animals of different species (among them mice and rats) by intravenous (iv.) bolus injection. The duration of this bolus injection had been set to 2 minutes to ensure that the exposure to the Prodrug (Compound 1) as well as to the Drug (Compound 2) is as high as possible for a given dose.

According to the principles of the distribution of a drug within the blood circulation during and after its iv. bolus injection, the maximum plasma concentration (Cmax) of the Prodrug (Compound 1) has been observed at the end of the bolus injection. Moreover, according to the results derived from all the respective studies in animals it was concluded that the Drug (Compound 2) is very rapidly generated from the Prodrug (Compound 1): In all studies Cmax of the Drug (Compound 2) was observed at the very first sampling time (i.e. <5 min after the end of the iv. bolus injection).

To establish the highest exposure possible also in humans, a study with Compound 1 has been designed. Therefore, ascending Prodrug (Compound 1) doses considered safe have been administered to 38 healthy Caucasian male volunteers by 2 min iv. bolus injections in the First-in-Man study.

Volunteers were administered doses of up to 3.0 mg/kg body weight (BW) of Compound 1 given as iv. bolus injection of 2 min duration. Additionally, doses of 1.5 and 3.0 mg/kg BW of Compound 1 were administered as a short-term infusion of 20 min duration, resulting in infusion rates of 4.5 and 9.0 mg/(kg BW×h), respectively.

As observed in all animal species investigated, also in humans there was very rapid conversion of the Prodrug (Compound 1) to the Drug (Compound 2) at all doses applied; Cmax of the Drug (Compound 2) was already observed 10 min after iv. bolus administration of the Prodrug.

These observations led to the assumption that a prolongation of the duration of the iv. administration from the 2 min bolus to a short-term infusion of 20 min cannot result in any further improvement of the conversion of the Prodrug (Compound 1) into the Drug (Compound 2).

However, surprisingly, the exposure to the Drug (Compound 2) was much higher after the 20-min infusion (infusion rate 9 mg/(kg BW×h)) than after bolus administration of 3.0 mg/kg BW, i.e. 149% and 130% for the area under the curve (AUC) and the maximum concentration (Cmax), respectively (see table 1). For the 1.5 mg/kg BW dose infused over 20 min (infusion rate 4.5 mg/(kg BW×h)), the dose-normalized exposure data of the Drug (Compound 2) are even higher than those measured following the dose of 3 mg/kg BW regardless if administered as iv. bolus or 20 min infusion (see table 1).

TABLE 1

Mean exposure data of the Drug (Compound 2) after intravenous administration of 3.0 mg/kg BW Prodrug (Compound 1) as bolus, or after 20 min infusions of 3.0 or 1.5 mg/kg BW at an infusion rate of 9.0 and 4.5 mg/(kg BW × h), respectively.

| Dose [mg/kg BW] | Infusion Rate [mg/(kg BW · h)] | AUC [µg · h/L] | Ratio infusion/ bolus [%] | Cmax [µg/L] | Ratio infusion/ bolus [%] |
|---|---|---|---|---|---|
| 3.0 | bolus | 2174 | | 2449 | |
| 3.0 | 9.0 | 3234 | 149 | 3175 | 130 |
| 1.5 | 4.5 | 5622* | 259 | 4924* | 201 |

*value normalized to a dose of 3.0 mg/kg BW

Accordingly, a dose of 1.5 mg/kg BW infused at a rate of 4.5 mg/(kg BW×h) resulted in a similar exposure compared to a dose of 3.0 mg/kg BW infused at a rate of 9.0 mg/(kg BW×h).

For the Prodrug (Compound 1), the prolongation of the administration of 3.0 mg/kg BW to 20 min infusion resulted in a lower AUC compared to bolus administration, because of the more efficient conversion to the Drug (Compound 2).

Considering the results of the First-in-Man study the effect of the infusion rate on the efficacy of the conversion of the Prodrug (Compound 1) into the Drug (Compound 2) has been investigated in a systematic manner.

In this clinical study the Prodrug (Compound 1) was administered to 30 healthy Caucasian male volunteers at infusion rates ranging between 0.4 and 3.0 mg/(kg BW×h). This range of infusion rates has been realised by combining different doses (1-6 mg/kg BW) with different durations of infusion (20-720 min).

Accordingly, it was possible to evaluate 3 Cohorts (groups) of volunteers each of which were infused at a range of infusion rates resulting from the different doses and infusion durations applied to this group.

The ratio of the AUC-values of the Drug vs. the Prodrug (Compound 2/Compound 1) was used as a measure of the conversion efficacy. The infusion rates of the respective Cohort and the resulting ratios are given in table 2; the higher the ratio, the more efficient the conversion of the Prodrug (Compound 1) into the Drug (Compound 2).

TABLE 2

Infusion rates applied to the Cohorts of volunteers and resulting AUC ratios Compound 2/Compound 1

| Infusion Rate [mg/(kg BW · h)] | Mean ratio |
|---|---|
| Cohort 1 | |
| 3.00 | 0.65 |
| 1.50 | 0.72 |
| 0.75 | 0.86 |
| Cohort 2 | |
| 1.50 | 0.75 |
| 0.75 | 0.83 |
| 0.40 | 0.62 |
| Cohort 3 | |
| 0.50 | 0.65 |
| 0.50 | 0.60 |
| 0.50 | 0.63 |

In general, the mean ratios of AUC Compound 2/Compound 1 ranged between 0.86 and 0.60. It has been observed that the ratios were similar at identical infusion rates even if the doses administered are different.

Within Cohort 1 there was a steady increase of the mean ratio from 0.65 to 0.86 with decreasing infusion rate from 3 to 0.75 mg/(kg BW×h). Within Cohort 2 there was an increase of the mean ratio from 0.75 to 0.83 while the infusion rate decreased from 1.5 to 0.75 mg/(kg BW×h). The lowest infusion rate of 0.4 mg/(kg BW×h) in Cohort 2 showed a ratio of 0.62 and did not differ from the ratios observed in Cohort 3 at the infusion rate of 0.5 mg/(kg BW×h), ranging very consistently between 0.60 and 0.65.

Accordingly, by means of a systematic pharmacokinetic study performed in humans it was found that an infusion rate between 0.4 and 3 mg/(kg BW×h) is a preferred range with respect to the maximum amount of the Drug (Compound 2) generated from the infused Prodrug (Compound 1).

Moreover, for a given dose infused, the safety and tolerability improves with decreasing infusion rate.

Accordingly, an infusion rate between 0.4 and 0.75 mg/(kg BW×h) is especially preferred.

Example 2 (Treatment of Intestinal Diseases)

Healthy human volunteers received i.v. infusions of Compound 1 at a dose of 6 mg/kg body weight over 12 hours for 5 consecutive days. On Day 5, all volunteers had fecal concentrations of Compound 2, ranging between 98 and 226 mg/kg feces. These fecal concentrations of Compound 2 translated into marked effects on the Gram-positive aerobic and anaerobic microflora. The reduction of viable counts of *Clostridium* spp. from predose to Day 5 was 3.0 log 10 CFU/g, and viable counts were reduced below the limit of detection until Day 3 postdose in all except one of the volunteers. Viable counts of lactobacilli were reduced from predose to Day 5 by 4.0 log 10 CFU/g. The effect of Compound 2 on bifidobacteria was most pronounced: Viable counts were reduced from predose to Day 5 by 7.9 log 10 CFU/g. Likewise, enterococci were reduced from predose to Day 5 by 3.8 log 10 CFU/g on average. Exposure of the fecal flora to MCB3681 did not affect the Gram-negative species.

Evaluation of the Activity of Compound 2 Against *Clostridium difficile*:

One hundred fourteen *Clostridium difficile* strains were collected from 67 patients and analyzed for the presence of *C. difficile* toxin B by the cell cytotoxicity neutralization assay, genes for toxin A, toxin B, binary toxin and TcdC deletion by PCR. All strains were also PCR-ribotyped. The MICs of the isolates were determined against Compound 2 by the agar dilution method. All isolates were positive for toxin B. One hundred thirteen isolates were positive for toxin A and B genes. In addition, 13 isolates were positive for the binary toxin genes. Thirty-two different ribotypes were identified. No strain of ribotype 027 was found. All 114 isolates were sensitive to Compound 2 (MIC range 0.008-0.5 mg/1). Accordingly, Compound 2 has a potent in vitro activity against *C. difficile*.

1. Materials and Methods:
1.1. Collection and Typing of Strains

One hundred fourteen *C. difficile* strains were selected from patients (26 males and 41 females) with primary and/or recurrent CDI. The mean age of the patients was 74 years (age range 19-97 years). The strains (67 primary and 47 recurrent isolates) were identified by characteristic colony morphology, typical smell and Gram staining. Gas chromatography was used to detect volatile, short chain fatty acids production by the *C. difficile* strains for the final identification.

1.2. Toxin and Toxin Gene Detection

The production of toxin B was determined by the cell cytotoxicity neutralization assay. The gene for toxin A was detected by conventional PCR [Kato H, Kato N, Watanabe K, Iwai N, Nakamura H, Yamamoto T, et al. Identification of toxin A-negative, toxin B-positive *Clostridium difficile* by PCR. J Clin Microbiol 1998; 36:2178-82]. The genes for toxin B, the binary toxin and TcdC deletion were detected by real time PCR using the GeneXpert® System (Cepheid, Sunnyvale, Calif., USA) assay [Huang H, Weintraub A, Fang H, Nord C E. Comparison of a commercial multiplex real-time PCR to the cell cytotoxicity neutralization assay for diagnosis of *Clostridium difficile* infections. J Clin Microbiol 2009; 47:3729-31].

1.3. Ribotyping

PCR ribotyping and electrophoresis of the gels were performed with a method described previously [Stubbs S L, Brazier J S, O'Neill G L, Duerden B I. PCR targeted to the 16S-23S rRNA gene intergenic spacer region of *Clostridium difficile* and construction of a library consisting of 116 different PCR ribotypes. J Clin Microbiol 1999; 37:461-3; Rashid M U, Lozano H M, Weintraub A, Nord C E. In vitro activity of cadazolid against *Clostridium difficile* strains isolated from primary and recurrent infections in Stockholm, Sweden. Anaerobe 2013; 20:32-5]. The gels were scanned and analyzed by Bionumerics software version 6.6. (Applied Maths, Kortrijk, Belgium). A molecular size standard (100 bp; GE Healthcare, Little Chalfont, Buckinghamshire, UK) was run at four to five lane intervals in all gels to enable normalization of the gel patterns. In every gel two known PCR ribotypes (005 and 012) were run as controls. The banding patterns were compared to a database including *C. difficile* reference strains. The stability, reliability and homogeneity of the database banding patterns constituting each type was tested with the cluster correlation algorithm with the unweighted pair group method by using arithmetic averages and fine alignment.

1.4. Antimicrobial Susceptibility

The antimicrobial susceptibility of the *C. difficile* strains was determined according to CLSI guidelines by the agar dilution method using *Bacteroides fragilis* ATCC 25285 and *C. difficile* ATCC 700057 as reference strains [CLSI. Methods for Antimicrobial Susceptibility Testing of Anaerobic Bacteria; Approved Standard-Eighth Edition. 2012]. Compound 2 was prepared as described in WO 2005/058888.

MIC was defined as the lowest concentration of the drug that inhibited growth completely. $MIC_{50/90}$ corresponds to the concentrations that inhibit the growth of 50% and 90% of the strains tested, respectively.

1.5. Statistical Methods

PCR ribotype profiles from clinical isolates were compared to those profiles which define the database by maximum matching with Pearson correlation. IBM SPSS Statistics 22 (Armonk, N.Y., USA) software was used to calculate the percentiles 50 and 90 of the MIC results. Descriptive statistics were used to summarize the results.

2. Results
2.1. Toxin Detection

The 114 strains were positive for toxin B by cell cytotoxicity neutralization assay. One hundred thirteen strains were positive for the genes of both toxin A and B. In addition, 13 strains were positive for the binary toxin genes. All strains were negative for TcdC deletion.

2.2. Ribotypes

Thirty-two different ribotypes were identified (Table 1). The ribotypes for the 13 strains positive for the genes of toxin A, toxin B and binary toxin were 023, 075, 078/126 and 019. One strain did not match with any of the known ribotypes and was a cluster of SE 91. The most common ribotypes were 020 (14.9%), 014/077 (8.8%), 078/126 (7%), 001 (6.1%) and 026 (6.1%). No ribotype 027 was found among any of the isolates.

TABLE 1

Thirty two different PCR-ribotypes of the 114 *C. difficile* strains.

| Ribotype | Number of strains |
|---|---|
| 020 | 17 |
| 014/077 | 10 |
| 078/126 | 8 |
| 001 | 7 |
| 026 | 7 |
| SE14 | 6 |
| SE21 | 6 |
| 005 | 5 |
| SE2 | 5 |
| 023 | 4 |
| 207 | 4 |
| 002 | 3 |
| 231 | 3 |
| SE23a | 3 |
| SE35 | 3 |
| 012 | 2 |
| 017 | 2 |
| 075 | 2 |
| SE23b | 2 |
| SE36 | 2 |
| SE46 | 2 |

One strain each of ribotypes 003, 019, 029, 046, 087, SE14b, SE20d, SE24, SE48, SE49 and SE91 cluster ribotypes were identified.

2.3. Antimicrobial Susceptibility

The antimicrobial susceptibility patterns are shown in Table 2. All strains were sensitive to Compound 2 with $MIC_{90}$ values of 0.064 mg/l. None of the 114 *C. difficile* strains were resistant against Compound 2.

TABLE 2

Minimum inhibitory concentrations of 114 *C. difficile* strains against Compound 2.

| $MIC_{50}$ (mg/l) | $MIC_{90}$ (mg/l) | Range (mg/l) |
|---|---|---|
| 0.032 | 0.064 | 0.008-0.5 |

The invention claimed is:

1. A method for treating a bacterial infection caused by *Clostridium difficile*, comprising administering to a patient in need thereof a compound, which is 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

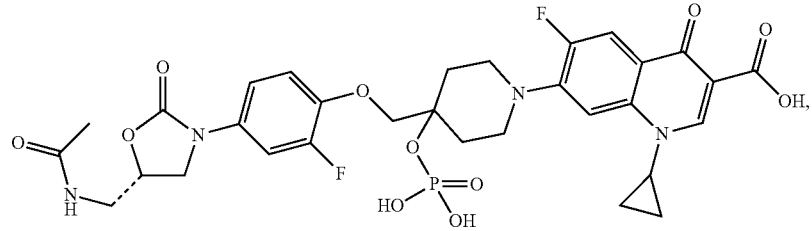 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

or a pharmacologically acceptable salt thereof.

2. The method according to claim 1, wherein the compound, or a pharmacologically acceptable salt thereof, is administered by an infusion.

3. The method according to claim 2, wherein the compound, or a pharmacologically acceptable salt thereof, is administered at an infusion rate of from 0.4 to 3 mg/(kg body weight×h).

4. The method according to claim 3, wherein the compound, or a pharmacologically acceptable salt thereof, is administered at an infusion rate of from 0.4 to 1.5 mg/(kg body weight×h).

5. The method according to claim 4, wherein the compound, or a pharmacologically acceptable salt thereof, is administered at an infusion rate of from 0.4 to 0.75 mg/(kg body weight×h).

6. The method according to claim 5, wherein the compound, or a pharmacologically acceptable salt thereof, is administered at an infusion rate of 0.5 mg/(kg body weight×h).

7. The method according to claim 1, wherein the compound, or a pharmacologically acceptable salt thereof, is administered over a period of from 20 min to 24 h per day.

8. The method according to claim 7, wherein the compound, or a pharmacologically acceptable salt thereof, is administered over a period of from 4 h to 12 h per day.

9. The method according to claim 8, wherein the compound, or a pharmacologically acceptable salt thereof, is administered over a period of 12 h per day.

10. The method according to claim 1, wherein the compound, or a pharmacologically acceptable salt thereof, is administered daily for a period of up to 10 days.

11. The method according to claim 10, wherein the compound, or a pharmacologically acceptable salt thereof, is administered daily for a period of 10 days.

12. The method according to claim 1, wherein the compound, or a pharmacologically acceptable salt thereof, is administered daily at a dose of 6 mg/kg.

13. The method according to claim 1, wherein the compound, or a pharmacologically acceptable salt thereof, is a sodium salt of the compound.

14. The method according to claim 1, wherein the bacterial infection caused by *Clostridium difficile* is an intestinal disease caused by *Clostridium difficile*.

15. The method according to claim 14, wherein the intestinal disease caused by *Clostridium difficile* is diarrhea, colitis, or pseudomembranous colitis.

16. The method according to claim 1, wherein the bacterial infection caused by *Clostridium difficile* is ileus, toxic megacolon, fulminant colitis, colonic perforation or need for colectomy.

17. A method for treating an intestinal disease caused by *Clostridium difficile*, comprising administering to a patient in need thereof a compound, which is 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

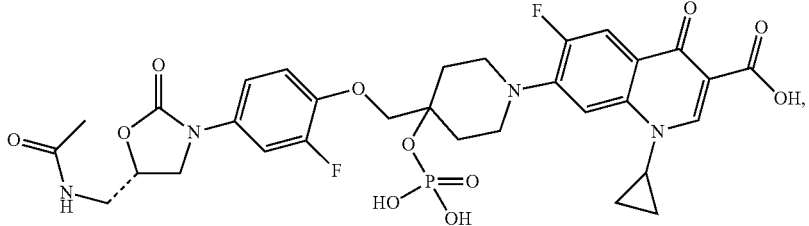 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

or a pharmacologically acceptable salt thereof, wherein the compound, or a pharmacologically acceptable salt thereof, is administered daily at an infusion rate of 0.5 mg/(kg body weight×h) over a period of 12 h per day for a period of 10 days.

18. The method according to claim 17, wherein the intestinal disease caused by *Clostridium difficile* is diarrhea, colitis, or pseudomembranous colitis.

19. The method according to claim 17, wherein the intestinal disease caused by *Clostridium difficile* is ileus, toxic megacolon, fulminant colitis, colonic perforation or need for colectomy.

20. The method according to claim 17, wherein the compound, or a pharmacologically acceptable salt thereof, is a sodium salt of the compound.

* * * * *